United States Patent [19]

L'Orange

[11] 4,001,393
[45] Jan. 4, 1977

[54] MEANS FOR CARIES PROPHYLAXIS

[75] Inventor: Raul L'Orange, Mainz, Germany

[73] Assignee: Blendax-Werke R. Schneider GmbH & Co., Germany

[22] Filed: Jan. 9, 1974

[21] Appl. No.: 431,856

[30] Foreign Application Priority Data

Jan. 20, 1973 Germany .......................... 2302812

[52] U.S. Cl. .................................. 424/52; 424/54
[51] Int. Cl.$^2$ ...................... A61K 7/18; A61K 7/22
[58] Field of Search ............................. 424/49–58, 424/326; 260/565

[56] References Cited

UNITED STATES PATENTS

| | | | |
|---|---|---|---|
| 2,684,924 | 7/1954 | Rose et al. ........................ | 424/326 |
| 2,863,919 | 12/1958 | Birtwell et al. ..................... | 260/565 |
| 2,990,425 | 6/1961 | Senior ........................... | 424/326 X |
| 3,152,181 | 10/1964 | Shapiro et al. ..................... | 424/52 |
| 3,887,712 | 6/1975 | Lover et al. ....................... | 424/326 |

FOREIGN PATENTS OR APPLICATIONS

| | | | |
|---|---|---|---|
| 233,215 | 6/1959 | Australia ........................... | 424/54 |
| 825,577 | 12/1959 | United Kingdom ................. | 424/54 |

OTHER PUBLICATIONS

Rose et al. (II) J. Chem. Soc. pp. 4422–4425 (1956) "Bis Biguanides Having Antibacterial Activity".
Gjermo et al. J. Periodont. Res. 8: Suppl. 12: 81–88 (1973) "Effect on Dental Plaque Formation and Some in Vitro Properties of 12 Bis–Biguanides".
Warner et al. J. Med. Chem. 16(6): 732–733 (1973) "1,6–bis(N$^5$–m–trifluoromethyl-phenyl–N'–biguanido)–hexane and Relates Analogs of Chlorhexidine as Inhibitors of Dental Plaque".
Chem. Abst. 71 No. 59413f (1969); 75 No. 47428j, No. 74792e (1971); 78 No. 33814g; No. 52942p No. 102001d (1973); 79 No. 87586y; 79 No. 111547j (1973); 80 No. 52342j, 55883x, 128097f (1974).

*Primary Examiner*—Shep K. Rose
*Attorney, Agent, or Firm*—Connolly and Hutz

[57] ABSTRACT

Disclosed are compositions containing 1,6-di-4'-fluoro-phenyldiguanidohexane and/or its non-toxic inorganic or organic salts as a means for caries prophylaxis.

10 Claims, No Drawings

MEANS FOR CARIES PROPHYLAXIS

FIELD OF THE INVENTION AND STATE OF THE ART

The present invention relates to an agent having an excellent caries-prophylactic effectiveness, which may be employed in various forms such as in dental care products including toothpastes, gels, mouthwashes, tooth powders, tooth cleaning, sucking, or chewing tablets or dragees or it may be added to foodstuffs or to drinking water.

Numerous agents have already been proposed for combatting or preventing the occurrence of dental caries. Among these compounds, those containing fluorine in ionic or complexbound form have received most attention, since the cariesprotective effectiveness of the element fluorine can be considered certain in view of innumerable clinical findings and animal tests. The most effective fluorine compounds have been shown to be sodium fluoride, tin fluoride and sodium monofluorophosphate.

It has also been proposed to use 1,6-di-4'-chlorophenyldiguanidohexane, known under the trivial name "chlorohexidine", and the non-toxic salts thereof as a caries prophylactic. The effectiveness of this substance, which also displays dental film or plaque removing or inhibiting properties is presumably based on its antibacterial effect against the oral microorganisms participating in the occurrence of caries. Because of this effect, chlorohexidine has already been added to dental care agents or drinking water. However, a distinct disadvantage in the use of chlorohexidine in caries prophylaxis has turned out to be its tendency to cause brown staining or discoloring of the teeth in repeated applications. Because of this unpleasant phenonmenon, there has so far been no practical utilization of the dental-film-inhibiting properties of chlorohexidine, such as by incorporating it in dental care agents as proposed, for example, by the German Patent No. 1,084,876.

BRIEF SUMMARY OF THE INVENTION

It has now been found that 1,6-di-4'-fluorophenyldiguanidohexane and the non-toxic inorganic or organic salts thereof have an excellent caries-prophylactic activity but do not exhibit the above-indicated disadvantageous properties of chlorohexidine. This fact is quite unexpected, since 1,6-di-4'-fluorophenyldiguanidohexane, which is also known under the trivial name "fluorohexidine" or under the nomenclature designation 5,5-di-p-fluorophenyl-1,1'-hexamethylenedibiguanidine, contrary to chlorohexidine, has practically no antibacterial activity and also it contains no free fluorine and, in an aqueous medium, produces no free fluorine.

DETAILED DESCRIPTION OF THE INVENTION

In the event the caries-prophylactic agent of the present invention is to be included in a dental care composition in an aqueous base or contained in drinking water, the use of a non-toxic, organic or inorganic, water-soluble fluorohexidine salt is preferred. For such use, fluorohexidine digluconate is particularly suitable and preferred. One may also use other water-soluble salts including the diacetate, dipropionate, diformiate, dilactate, dihydrochloride, dihydrofluoride, dibromide, sulfate, phosphate, succinate, pivalate, citrate, tartrate, maleate or malate salts. Generally, the active agent of the present invention is fluorohexidine and any salt-forming radical can be used where desired provided, of course, that it is non-toxic under the application conditions employed.

The caries-prophylactic effect of fluorohexidine is demonstrated in the following animal tests:

Two groups, A and B, of 5 Syrian hamsters were put on a carbohydrate-rich diet. Group A served as the control group and received normal drinking water, while the drinking water of Group B was mixed with fluorohexidine gluconate (0.1% fluorohexidine). After 3 months, the number of cavities in each group of animals was determined. The result was that the total number of cavities in the animals of Group A was 170 while in the animals of Group B only 16 cavities were noted. This clearly demonstrates the unexpected caries-prophylactic effectiveness of fluorohexidine.

The concentration of fluorohexidine or its salts in the novel composition for caries prophylaxis may be varied within wide limits and depends primarily on whether the agent is intended for daily regular use or as a periodically applied agent. In dental and oral care compositions used daily, the concentration is preferably between 0.01 and about 7.5% by weight of the total composition (calculated on free fluorohexidine); in periodically dispensed preparations, it may also be higher, suitably at about 0.5 to about 10.0% by weight (calculated on free fluorohexidine). Generally, a minimum amount of the active ingredient will be employed for reasons of economy but in any event the amount employed will be a caries-prophylactic amount.

A particularly suitable form of application is in the customary dental and oral care composition well known in the art which generally comprise a suitable carrier and the active ingredient of the present invention. Such compositions may be in the form of toothpastes, which may contain the customary polishing, binding, thickening and moisture-holding agents. Suitable polishing agents, which may be used even when the novel agent for the caries prophylaxis is present in the form of a tooth powder, are the various known calcium phosphates, for example, particularly dicalcium phosphate in the form of its anhydride or its dihydrate, calcium pyrophosphate, tricalciumphosphate, calcium carbonate, insoluble alkali metaphosphates such as sodium or potassium polymetaphosphate, aluminum oxide or its trihydrate, magnesium carbonate, silicon dioxide, aluminum or zirconium silicate, pulverulent synthetic substances such as polymethylmethacrylate, polyamides, melamine or urea formaldehyde condensation products or epoxy resins and compositions of the enumerated substances together or with other known polishing agents.

The novel preparations for caries prophylaxis may also be present in the form of a transparent or translucent gel with or without a content of polishing substances. The preferred carrier materials in this connection are alkali salts of polyacrylic acid, various cellulose derivatives, particularly carboxymethyl cellulose, Irish moss, tragacanth, galactomannan, and various plant mucilages. The above carrier materials may also be employed as binding agents in conventional toothpastes.

As gel formers and simultaneous polishing agents in toothpastes, preferably suitable are dehydrated silicon dioxide gels with a particle size of about 3 to about 20 microns, which are sold by the company Grace GmbH, Bad Homburg, under the trade name "Syloid". Suitable moisture-holding agents or humectants in toothpastes are particularly glycerin and sorbitol, but other sugar alcohols such as mannitol or lower aliphatic diols such as propane diol and butane diol have also been shown to be applicable in toothpastes. Toothpastes and mouthwashes customarily contain surface-active substances. As such, particularly the salts of higher alkyl sulfates, e.g., sodium lauryl sulfate, salts of higher aliphatic acylamides of lower aliphatic amino acids, e.g., N-lauroyl sarcosinate, albumin-fatty-acids condensate, nonionic surface active agents such as ethylene oxide condensates, quaternary ammonium compounds, e.g., cetyl trimethylammonium chloride or diisobutyl phenoxy ethoxy ethyl dimethybenzylammonium chloride, or ampholytic surface active agents, e.g., betains or long-chain alkylaminocarboxylic acids.

Toothpastes, tooth powder, mouthwash and other dental care compositions normally contain preserving agents, e.g., p-hydroxybenzoic acid ester, bromochlorophene, o-hydroxydiphenyl ether, sorbic acid, carbanilide or halogenated salicylic acid anilides and such may be used in the present invention.

The oral care products of the present invention as a rule also contain flavoring agents and aromatic substances. Suitable flavoring agents include saccharin sodium and sodium cyclamate for example; the applicable aromatic compositions are well known in the art and extremely numerous, and need not be enumerated here in more detail.

In addition to the content of fluorohexidine and/or the non-toxic salts thereof, the caries prophylaxis compositions of the present invention may contain still other effective substances known per se for use in dental and oral care agents. Aside from enzymes, these agents are, for example, dextranase, inorganic and organic phosphates, complex formers for calcium and magnesium, e.g., hydroxyethane diphosphonic acid, and vitamins, particularly the numerous fluorine compounds previously suggested for caries prophylaxis such as sodium fluoride, manganese fluoride, short and long-chain aminofluorides, etc.

The novel compositions of the present invention used for caries prophylaxis may be utilized not only as dental and oral care agents in the form of toothpastes, tooth powders, mouthwashes, tooth cleaning tablets and chewing gum but also in the form of chewing or sucking dragees and tablets, as high-percent brush-on solutions or gels for occasional domestic application or for use in medical practice. The addition to drinking water or to various foodstuffs is also possible.

The present invention is illustrated below in more detail by means of the following examples, it being understood that such examples are for illustration only and do not limit the scope of the instant invention. The numerical data recited in these examples refer to percent by weight unless otherwise stated.

EXAMPLE 1

| Toothpaste | |
|---|---|
| dicalcium phosphate dihydrate | 40.00% |
| calcium carbonate | 5.00% |
| glycerin | 25.00% |
| sorbitol, 70% | 5.00% |
| sodium-N-lauroylsarcosinate | 1.50% |
| carboxymethylcellulose | 1.50% |
| p-hydroxybenzoic acid ester | 0.20% |
| saccharin sodium | 0.10% |
| sodium fluoride | 0.30% |

| -continued | |
|---|---|
| Toothpaste | |
| fluorohexidine digluconate | 0.50% |
| aroma | 0.20% |
| water | 20.70% |

EXAMPLE 2

| Tooth Gel | |
|---|---|
| dehydrated silicon dioxide xerogel (average particle size 9 microns, 700 m$^2$/g surface) | 20.00% |
| dehydrated silicon dioxide aerogel (average particle size 9 microns, 700 m$^2$/g surface) | 5.00% |
| glycerin | 35.00% |
| sorbitol, 70% | 15.00% |
| hydroxyethyl cellulose | 1.50% |
| polyethylene glycol 600 | 3.50% |
| sodium lauryl sulfate | 1.20% |
| bromochlorphene | 0.10% |
| p-hydroxybenzoic acid ester | 0.15% |
| sodium monofluorophosphate | 0.75% |
| fluorohexidine diacetate | 0.80% |
| aromatic and flavoring substances | 1.00% |
| water | 16.00% |

EXAMPLE 3

| Mouthwash | |
|---|---|
| sodium lauryl sulfoacetate | 1.50% |
| glycerin | 15.00% |
| hexetidine | 0.15% |
| aromatic and flavoring substances | 1.15% |
| fluorohexidine digluconate | 2.20% |
| ethanol, 90% | 40.00% |
| water | 40.00% |

EXAMPLE 4

| Tooth Powder | |
|---|---|
| dicalciumphosphate dihydrate | 50.00% |
| dicalciumphosphate anhydride | 20.00% |
| polymethylmetacrylate powder | 15.00% |
| PVC, pulverulent | 8.00% |
| sodium lauryl sulfate | 1.50% |
| flavoring and aromatic substances | 1.00% |
| fluorohexidine dihydrochloride | 4.50% |

EXAMPLE 5

| Tooth-cleaning Tablets | |
|---|---|
| dicalciumphosphate | 60.00% |
| calcium carbonate | 10.00% |
| silicon dioxide (particle size 0.01 – 0.05 microns) | 15.00% |
| polyamide powder | 5.00% |
| polyvinyl pyrrolidone | 0.80% |
| flavoring and aromatic substances | 2.20% |
| tragacanth | 1.50% |
| sodium lauryl sulfate | 2.50% |
| fluorohexidine dihydrochloride | 3.00% |

EXAMPLE 6

Chewing Gum

Into basic chewing gum mass of a customary composition were additionally worked in 3.5 parts by weight fluorohexidine diacetate and 0.75 parts by weight Na$_2$-

$PO_3F$ per 100 parts of the total composition, the substance was mixed, rolled out and cut in strips.

EXAMPLE 7

| Brush-on Solution for Occasional Application by a Dentist | |
|---|---|
| fluorohexidine digluconate | 7.5% |
| water | 92.5% |

In a similar manner, the fluorohexidine may also be added to candy, dragees, chewing tablets, foodstuffs, e.g., common salt, or also drinking water.

What is claimed is:

1. A composition effective in preventing caries comprising a non-toxic carrier substance and a caries-prophylactic amount of a member selected from the group consisting of 1,6-di-4'-fluorophenyldiguanidohexane, its non-toxic salts and mixtures thereof.

2. The composition according to claim 1 in the form of a dental and oral care composition wherein the carrier substance is at least one member selected from the group consisting of a polishing agent, a binding and thickening agent, a moisture-holding agent and a surface active agent.

3. The composition according to claim 1 wherein the member selected from the group consisting of 1,6-di-4'-fluorophenyldiguanidohexane, its salts and mixtures thereof is present in an amount of from about 0.01 to about 7.5 percent by weight of the total composition.

4. The composition according to claim 2 in the form of a member selected from the group consisting of toothpaste, tooth powder, mouthwash, tooth gel and chewing gum.

5. The composition according to claim 1 in the form of a member selected from the group consisting of a dragee, a tablet and candy.

6. The composition according to claim 4 wherein a member selected from the group consisting of the digluconate and the diacetate of 1,6-di-4'-fluorophenyl-diguanidohexane is used.

7. The composition according to claim 1 in the form of a composition for topical application to teeth, the content of the member selected from the group consisting of 1,6-di-4'-fluorophenyldiguanidohexane, its salts and mixtures thereof being from about 0.5 to about 10% by weight of the total composition.

8. A method of reducing caries in teeth which comprises contacting the teeth with a composition according to claim 1.

9. A method of reducing caries in teeth which comprises contacting the teeth with a composition according to claim 4.

10. A method of reducing caries in teeth which comprises contacting the teeth with a composition according to claim 6.

* * * * *